US009828626B2

(12) United States Patent
Ahmad et al.

(10) Patent No.: US 9,828,626 B2
(45) Date of Patent: Nov. 28, 2017

(54) DENDRIMER CONJUGATES FOR DETERMINING MEMBRANE RETENTION LEVEL AND/OR PORE STRUCTURE

(71) Applicant: Pall Corporation, Port Washington, NY (US)

(72) Inventors: Farhan Ahmad, Hicksville, NY (US); Jian M. Qiu, Oakland Gardens, NY (US); Amarnauth Singh, Selden, NY (US); Barbara Mish, Huntington, NY (US)

(73) Assignee: Pall Corporation, Port Washington, NY (US)

( * ) Notice: Subject to any disclaimer, the term of this patent is extended or adjusted under 35 U.S.C. 154(b) by 312 days.

(21) Appl. No.: 14/796,150

(22) Filed: Jul. 10, 2015

(65) Prior Publication Data

US 2017/0009290 A1 Jan. 12, 2017

(51) Int. Cl.
*C12Q 1/68* (2006.01)
*B01D 65/10* (2006.01)
*G01N 15/08* (2006.01)

(52) U.S. Cl.
CPC ............ *C12Q 1/68* (2013.01); *B01D 65/102* (2013.01); *G01N 15/08* (2013.01); *G01N 2015/086* (2013.01)

(58) Field of Classification Search
None
See application file for complete search history.

(56) References Cited

U.S. PATENT DOCUMENTS

| 4,713,975 | A | 12/1987 | Tomalia et al. |
| 4,925,572 | A | 5/1990 | Pall |
| 5,282,380 | A | 2/1994 | Dileo et al. |
| 6,365,415 | B1 | 4/2002 | Li et al. |
| 6,821,771 | B2 | 11/2004 | Festoc |
| 7,682,789 | B2 | 3/2010 | Chen et al. |
| 7,732,216 | B2 | 6/2010 | Nochumson et al. |
| 8,765,369 | B2 | 7/2014 | Dubus et al. |
| 2003/0143604 | A1 | 7/2003 | Storhoff et al. |
| 2003/0214066 | A1* | 11/2003 | Kools ............... B01D 67/0009 264/40.1 |
| 2008/0299672 | A1 | 12/2008 | Nochumson et al. |
| 2009/0220940 | A1 | 9/2009 | Lev et al. |
| 2012/0018313 | A1 | 1/2012 | Guigui et al. |

(Continued)

FOREIGN PATENT DOCUMENTS

| CN | 103990443 A | 8/2014 |
| WO | WO 98/04571 A2 | 2/1998 |
| WO | WO 2007/046095 A2 | 4/2007 |

(Continued)

OTHER PUBLICATIONS

Shchepinov et al. Oligonucleotide dendrimers: synthesis and use as polylabelled DNA probes. Nucleic Acids Research 25(22):4447-4454 (1997).*

(Continued)

*Primary Examiner* — Samuel C Woolwine
(74) *Attorney, Agent, or Firm* — Leydig Voit & Mayer

(57) ABSTRACT

Dendrimer conjugates for determining membrane retention level and/or pore structure, methods of determining membrane level/pore structure, and kits including dendrimer conjugates are disclosed.

20 Claims, 12 Drawing Sheets

(56) References Cited

U.S. PATENT DOCUMENTS

2012/0112097 A1   5/2012 Lee et al.

FOREIGN PATENT DOCUMENTS

| WO | WO 2011/106481 A1 | 9/2011 |
| WO | WO 2013/110458 A1 | 8/2013 |
| WO | WO 2014/012077 A1 | 1/2014 |
| WO | WO 2014/197455 A1 | 12/2014 |

OTHER PUBLICATIONS

Intellectual Property Office of Singapore, Search Report in counterpart Singapore Application No. 10201603298Y, dated Dec. 19, 2016.

European Patent Office, European Search Report in counterpart European Patent Application No. 16167110.2, dated Dec. 23, 2016.

Caminade, A., et al., "Dendrimers and DNA: Combinations of Two Special Topologies for Nanomaterials and Biology," *Chem. Eur. J.*, 14: 7422-7432 (2008).

Liu, H., et al., "DNA-Templated Covalent Coupling of G4 PAMAM Dendrimers," *J. Am. Chem. Soc.*, 132: 18054-18056 (2010).

Mizuno, T., et al., "A Novel Filter Rating Method Using Less Than 30-nm Gold Nanoparticle and Protective Ligand," *IEEE Transactions on Semiconductor Manufacturing*, 22(4): 452-461 (2009).

Gitis, V., et al., "Nanoscale probes for the evaluation of the integrity of ultrafiltration membranes", *Journal of Membrane Science*, 276, 199-207 (2006).

* cited by examiner

SEQUENCE LISTING

```
<160> NUMBER OF SEQ ID NOS: 8

<210> SEQ ID NO 1
<211> LENGTH: 66
<212> TYPE: DNA
<213> ORGANISM: Artificial Sequence
<220> FEATURE:
<223> OTHER INFORMATION: Synthetic sequence

<400> SEQUENCE: 1
cttgcaaatc gttctttggg tcctcttgcg accctgggag tgagcttgta tggttgacgc    60
cggatt                                                                66

<210> SEQ ID NO 2
<211> LENGTH: 20
<212> TYPE: DNA
<213> ORGANISM: Artificial Sequence
<220> FEATURE:
<223> OTHER INFORMATION: Synthetic sequence

<400> SEQUENCE: 2
cttgcaaatc gttctttggg                                                 20

<210> SEQ ID NO 3
<211> LENGTH: 19
<212> TYPE: DNA
<213> ORGANISM: Artificial Sequence
<220> FEATURE:
<223> OTHER INFORMATION: Synthetic sequence

<400> SEQUENCE: 3
aatccggcgt caaccatac                                                  19

<210> SEQ ID NO 4
<211> LENGTH: 25
<212> TYPE: DNA
<213> ORGANISM: Artificial Sequence
<220> FEATURE:
<223> OTHER INFORMATION: Synthetic sequence

<400> SEQUENCE: 4
cctcttgcga ccctgggagt gagct                                           25

<210> SEQ ID NO 5
<211> LENGTH: 73
<212> TYPE: DNA
<213> ORGANISM: Alicyclobacillus acidocaldarius

<400> SEQUENCE: 5
cttgctggac agtgactgac tccacgccgt aaacgatgag tgctaggtgt ggaaacccaa    60
taagcagtcc ggg                                                        73

<210> SEQ ID NO 6
```

```
<211> LENGTH: 20
<212> TYPE: DNA
<213> ORGANISM: Alicyclobacillus acidocaldarius

<400> SEQUENCE: 6
cttgctggac agtgactgac                                              20

<210> SEQ ID NO 7
<211> LENGTH: 23
<212> TYPE: DNA
<213> ORGANISM: Alicyclobacillus acidocaldarius

<400> SEQUENCE: 7
cccggagtgc ttattgggtt tcc                                          23

<210> SEQ ID NO 8
<211> LENGTH: 28
<212> TYPE: DNA
<213> ORGANISM: Alicyclobacillus acidocaldarius

<400> SEQUENCE: 8
ccacgccgta aacgatgagt gctaggtg                                     28
```

DENDRIMER CONJUGATES FOR DETERMINING MEMBRANE RETENTION LEVEL AND/OR PORE STRUCTURE

Incorporated by reference in its entirety herein is a computer-readable nucleotide/amino acid sequence listing submitted concurrently herewith and identified as follows: One 1,856 bytes ASCII (Text) file named "720484_ReplacementSeqListing_ST25.TXT created on Aug. 11, 2015.

BACKGROUND OF THE INVENTION

Tests such as leakage testing and gold particle testing can be used to determine membrane integrity. However, these tests can have drawbacks. For example, the gold particle test can have limited sensitivity due to limits of the instrumentation for detecting the gold particles and/or require a high challenge concentration of gold particles. Additionally, while integrity testing provides for determining whether a membrane has a large hole or tear, it does not provide for determining the membrane retention level or determining the pore structure to determine the pore size or rating.

The present invention provides for ameliorating at least some of the disadvantages of the prior art. These and other advantages of the present invention will be apparent from the description as set forth below.

BRIEF SUMMARY OF THE INVENTION

An embodiment of the invention provides a method for determining retention level and/or pore structure of a membrane, the method comprising (a) passing a challenge solution comprising single-stranded DNA conjugated to dendrimers (dendrimer conjugates), through a microporous membrane, to provide a permeate solution comprising the dendrimer conjugates; (b) obtaining equal volumes of: (i) the challenge solution comprising dendrimer conjugates; and, (ii) the permeate solution comprising dendrimer conjugates; (c) combining (i) with PCR reagents to provide a challenge solution/PCR mix, and combining (ii) with PCR reagents to provide a permeate solution/PCR mix; (d) performing a plurality of PCR cycles using each of the challenge solution/PCR mix, and the permeate solution/PCR mix, to amplify the single-stranded DNA; (e) measuring single-stranded DNA concentration, which correlates to dendrimer conjugate concentration; (f) quantifying the dendrimer conjugate concentration in the challenge solution (quantCo); and quantifying the dendrimer conjugate concentration in the permeate solution (quantCp); and, (g) determining the retention level and/or pore structure of the membrane based on a comparison of the quantCp to the quantCo.

BRIEF DESCRIPTION OF THE SEVERAL VIEWS OF THE DRAWING(S)

Figure 12A:
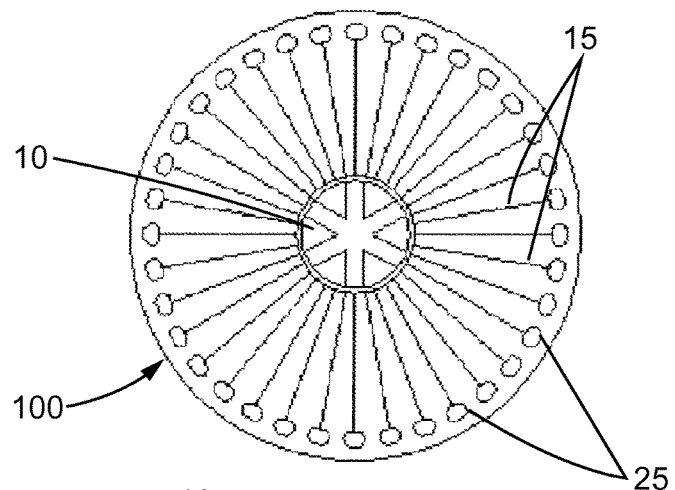
Figure 12B:
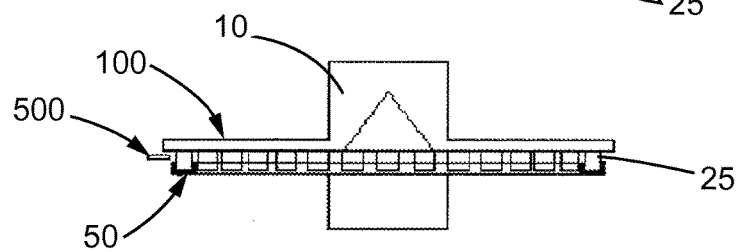
Figure 12C:
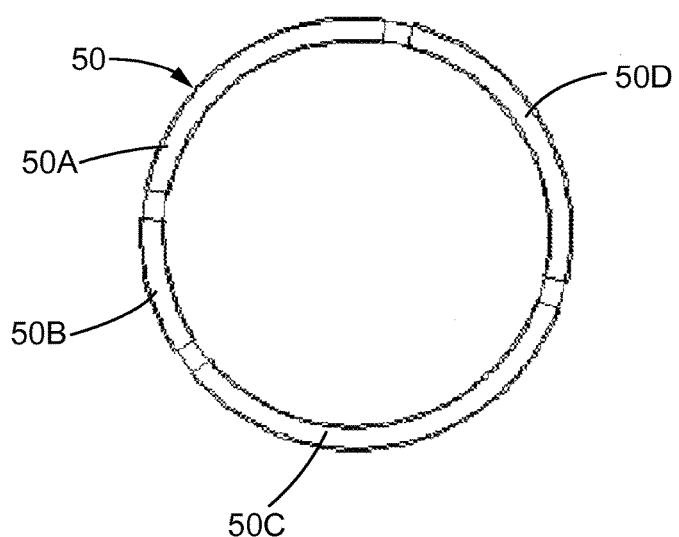

FIG. 12A, FIG. 12B, and and FIG. 12C show, respectively, a top view of a rotatable circular cartridge having a plurality of reaction chambers and a reservoir, wherein the reaction chambers are connected to the reservoir via channels, suitable for an exemplary PCR device that can be used for carrying out PCR cycles in accordance with embodiments of the invention; a cross-sectional side view of the cartridge arranged over a heating plate having a plurality of distinct zones that can be heated to different temperatures for carrying out PCR, and an illustrative heating plate having 4 distinct zones that can be heated to different temperatures for carrying out PCR.

DETAILED DESCRIPTION OF THE INVENTION

In accordance with an embodiment of the present invention, a method for determining retention level and/or pore structure of a membrane is provided, the method comprising (a) passing a challenge solution comprising single-stranded DNA conjugated to dendrimers (dendrimer conjugates), through a microporous membrane, to provide a permeate solution comprising the dendrimer conjugates; (b) obtaining equal volumes of: (i) the challenge solution comprising dendrimer conjugates; and, (ii) the permeate solution comprising dendrimer conjugates; (c) combining (i) with PCR reagents to provide a challenge solution/PCR mix, and combining (ii) with PCR reagents to provide a permeate solution/PCR mix; (d) performing a plurality of PCR cycles using each of the challenge solution/PCR mix, and the permeate solution/PCR mix, to amplify the single-stranded DNA; (e) measuring single-stranded DNA concentration, which correlates to dendrimer conjugate concentration; (f) quantifying the dendrimer conjugate concentration in the challenge solution (quantCo); and quantifying the dendrimer conjugate concentration in the permeate solution (quantCp); and, (g) determining the retention level and/or pore structure of the membrane based on a comparison of the quantCp to the quantCo. In a preferred embodiment, the PCR cycles are qPCR cycles.

Typically, determining the retention level and/or pore structure of the membrane based a comparison of the quantCp to the quantCo comparing log reduction values for quantCp and quantCo.

In some embodiments of the method, the dendrimer conjugates have a 1:1 ratio of single-stranded DNA to dendrimer.

If desired, embodiments of the method can comprise passing the challenge solution through the microporous membrane at a constant flow rate, or at a constant pressure.

While embodiments of the method, particularly with respect to performing PCR amplification, can be performed using a variety of devices, illustratively, within a device comprising a rotatable circular cartridge having a plurality of reaction chambers, and a reservoir, the reaction chambers being connected to the reservoir via channels, wherein at least a portion of the reaction chambers comprise primers; and a heating plate having at least two distinct zones that can be heated to at least two different temperatures, equal volumes of the challenge solution comprising dendrimer conjugates, and of the permeate solution comprising dendrimer conjugates, can each be combined with PCR reagents to provide, respectively, a challenge solution/PCR mix, and a permeate solution/PCR mix; and a plurality of PCR cycles can be performed using each of the challenge solution/PCR mix, and the permeate solution/PCR mix, to amplify the single-stranded DNA, an embodiment of the method can comprise at least partially filling the reservoir with a fluid containing dendrimer conjugates and PCR reagents for carrying out an amplification reaction, with the exception of primers; distributing the fluid to the reaction chambers comprising the primers therein; and, rotating the rotatable circular cartridge to successively bring the contents of each reaction chamber to the at least two temperatures defined by the at least two distinct zones of the heating plate, wherein the single-stranded DNA is amplified.

In some embodiments of the method, wherein the heating plate has at least three distinct zones that can be heated to at least three different temperatures, the method includes rotating the rotatable circular cartridge to successively bring the contents of each reaction chamber to the at least three temperatures defined by the at least three distinct zones of the heating plate.

In accordance with another embodiment, a kit is provided, the kit comprising a solution comprising a plurality of dendrimers conjugated to single-stranded DNA; a rotatable circular cartridge having a plurality of reaction chambers (containing dried primers and, preferably, dried probes) and a reservoir, wherein the reaction chambers are connected to the reservoir via channels; and a qPCR master mixture. In one embodiment of the kit, the qPCR master mixture comprises reference dye, polymerase, $MgCl_2$, and dNTPs.

Advantageously, in contrast with other tests requiring high levels of particles in the challenge solution due to limited sensitivity of the instrumentation for detecting particles (e.g., for detecting gold, silica, and latex particles, including inductively coupled plasma mass spectrometry (ICP-MS) particle counter instrumentation), tests can now be carried out using more realistic low particle challenge concentrations, e.g., about 1,000 to about 10,000 particles/mL, and very tight pore structure high performance membranes can be tested to determine only the sieving-based retention performance.

Dendrimers are repetitively branched molecules, typically highly symmetric spherical compounds, and can be considered to have three major portions: a core, an inner shell, and an outer shell. They can be classified by generation, which refers to the number of repeated branching cycles that are performed during its synthesis. Higher generation dendrimers also have more exposed functional groups on the surface. A variety of dendrimer particles are suitable for use in the invention, wherein the dendrimer can be, if desired, functionalized for conjugation to single-stranded DNA. Suitable functionalities include, for example, amino, hydroxyl, and/or succinamic acid functionality. Suitable dendrimers include, for example, commercially available dendrimers. In one embodiment, the dendrimer comprises a polyamidoamine (PAMAM) dendrimer, such as a $5^{th}$ generation PAMAM dendrimer.

Figure 1:
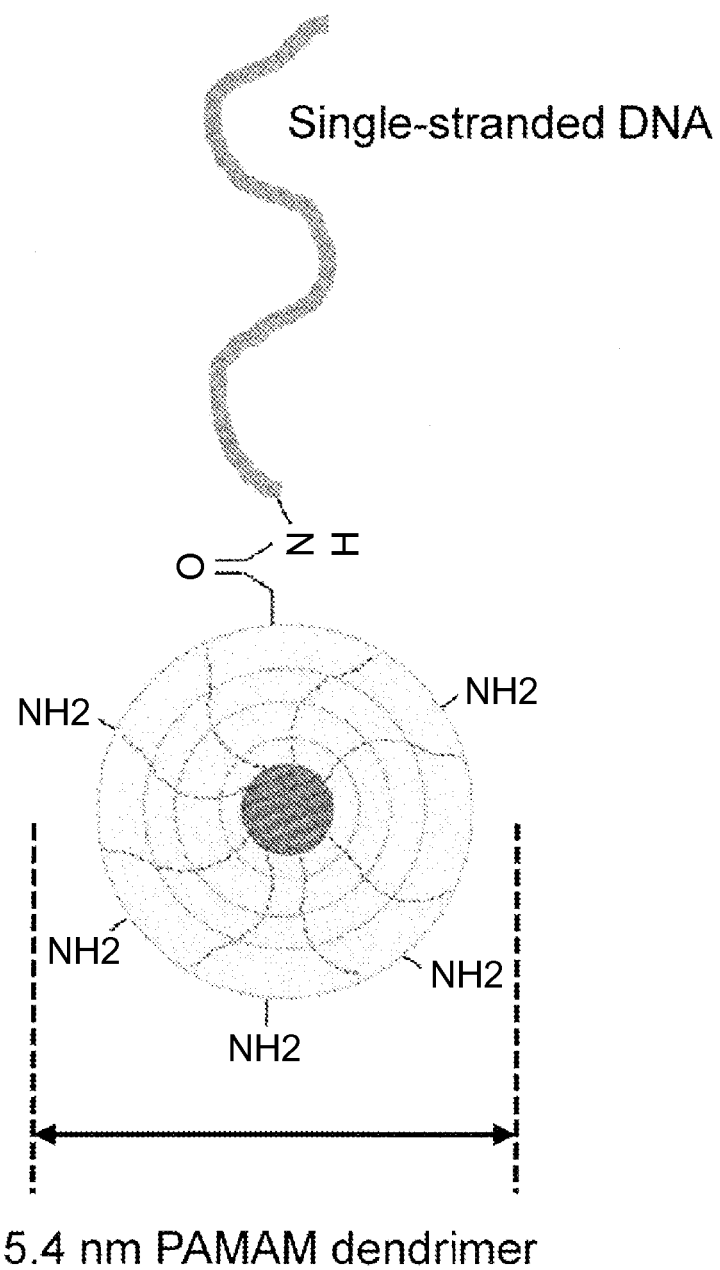
FIG. 1 shows an illustrative dendrimer conjugate comprising a dendrimer particle (illustrated as having a diameter of 5.4 nm) conjugated to single-stranded DNA by a covalent amide bond according to an embodiment of the present invention.

FIG. 1 illustrates a PAMAM dendrimer reacted with a carboxylic terminated single-stranded DNA sequence to immobilize the DNA on an amino functionalized dendrimer by a covalent amide bond.

The dendrimer particles can have any suitable diameter, typically, at least about 2 nm in diameter, though smaller diameter particles, preferably if available in monodisperse size diameter, can be used.

In accordance with embodiments of the invention, the single-stranded DNA is not limited to any particular sequence, or any particular number of bases. However, the sequence should be selected such that it is unlikely to be naturally present in the challenge solution, and typically, the single-stranded DNA is at least about 50 bases in length (e.g., for efficiency in amplification by qPCR).

The ratio of DNA to dendrimer should be such that it does not significantly change the size of the conjugate. Preferably, the ratio of DNA to dendrimer is 1:1, e.g., such that the PCR measured DNA concentration is directly correlatable to the concentration of dendrimer particles. However, ratios such as 10:1, or even higher, can also be used.

The presence of free-DNA (referred to below as "the free-DNA concentration") can affect the sensitivity of the method. For example, if a log removal value (LRV) of 4 or more is desired, it may be preferable to have a free-DNA concentration at a level of <0.001%; for a desired LRV of about 3, a free-DNA concentration at a level of about 0.01%; for desired LRV of about 2, a free-DNA concentration at a level of about 0.1%; and desired LRV of about 1, a free-DNA concentration at a level of about 1%.

Embodiments of the invention are especially suitable for use with aqueous solutions.

The membranes to be analyzed can have any retention level, e.g., a log removal rating (LRV) or a pore structure, e.g., a pore size (for example, as evidenced by bubble point, or by $K_L$ as described in, for example, U.S. Pat. No. 4,340,479, or evidenced by capillary condensation flow porometry), a mean flow pore (MFP) size (e.g., when characterized using a porometer, for example, a Porvair Porometer (Porvair plc, Norfolk, UK), or a porometer available under the trademark POROLUX (Belgium)), a pore rating, a pore diameter (e.g., when characterized using the modified OSU F2 test as described in, for example, U.S. Pat. No. 4,925,572), or removal rating media. The pore structure used depends on the size of the particles to be utilized, the composition of the fluid to be treated, and the desired effluent level of the treated fluid.

Embodiments of the invention are suitable for analyzing hydrophobic membranes and hydrophilic membranes.

A variety of membranes, especially polymeric membranes, are suitable for use in the invention, and are known in the art. Suitable polymers can include, for example, polyaromatics; sulfones (e.g., polysulfones, including aromatic polysulfones such as, for example, polyethersulfone (PES), polyether ether sulfone, bisphenol A polysulfone, polyarylsulfone (PAS), and polyphenylsulfone), polyamides, polyimides, polyvinylidene halides (including polyvinylidene fluoride (PVDF)), polyolefins, such as polypropylene and polymethylpentene, polyesters, polystyrenes, polycarbonates, polyacrylonitriles (including polyalkylacrylonitriles), cellulosic polymers (such as cellulose acetates and cellulose nitrates), fluoropolymers (such as, for example, polytetrafluoroethylene (PTFE)), and polyetherether ketone (PEEK). The polymeric membranes can include a mixture of polymers, e.g., a hydrophobic polymer (e.g., a sulfone polymer) and a hydrophilic polymer (e.g., polyvinylpyrrolidone).

The membrane, which can be hydrophobic or hydrophilic, can have any critical wetting surface tension (CWST, as defined in, for example, U.S. Pat. No. 4,925,572), and as additionally disclosed in, for example, U.S. Pat. Nos. 5,152,905, 5,443,743, 5,472,621, and 6,074,869.

Amplifying the DNA using the polymerase chain reaction (PCR), preferably, quantitative PCR (qPCR), can be carried out using devices and methods as known in the art. Suitable devices include, but are not limited to those available from Thermo Fisher Scientific Inc. (Applied Biosystems® 7900HT, 7300, 7500, 7500 fast, StepOne™ and StepOnePlus, QuantStudio®); Roche (LightCycler® 480, 96, 1536, Carousel, and Nano systems); Qiagen (Rotor-Gene Q™ systems); and Bio-Rad (CFX™ and Chromo™ systems).

One preferred device for carrying out PCR is described in U.S. Pat. No. 6,821,771 (that includes a rotatable circular cartridge having a plurality of reaction chambers, and a reservoir, the reaction chambers being connected to the reservoir via channels, and a heating plate having at least two, preferably, at least three, distinct zones that can be heated to at least two different temperatures), using, for example, GENEDISC plates available from Pall Corporation, Port Washington, N.Y., USA. FIGS. 12A, 12B, and 12C show, respectively, a top view of a rotatable circular cartridge 100 having a plurality of reaction chambers 25 and a reservoir 10, wherein the reaction chambers are connected to the reservoir via channels 15, suitable for an exemplary PCR device that can be used for carrying out PCR cycles in accordance with embodiments of the invention; a cross-sectional side view of the cartridge 100 arranged over a heating plate 50 having a plurality of distinct zones (50A, 50B, 50C, 50D) that can be heated to different temperatures for carrying out PCR, and an illustrative heating plate 50 having 4 distinct zones (50A, 50B, 50C, 50D) that can be heated to different temperatures for carrying out PCR. FIG. 12B also shows a detector 500, preferably a fluorescence detector, for detecting a signal (preferably a fluorescing dye) in the reaction chamber during PCR.

Illustratively, within a device comprising a rotatable circular cartridge having a plurality of reaction chambers, and a reservoir, the reaction chambers being connected to the reservoir via channels, wherein at least a portion of the reaction chambers comprise primers (preferably, the reaction chambers also comprise probes); and a heating plate having a plurality of distinct zones that can be heated to a plurality of different temperatures, equal volumes of the challenge solution comprising dendrimer conjugates, and of the permeate solution comprising dendrimer conjugates, can each be combined with PCR reagents to provide, respectively, a challenge solution/PCR mix, and a permeate solution/PCR mix; and a plurality of PCR cycles can be performed using each of the challenge solution/PCR mix, and the permeate solution/PCR mix, to amplify the single-stranded DNA, an embodiment of the method can comprise at least partially filling the reservoir with a fluid containing dendrimer conjugates and PCR reagents for carrying out an amplification reaction, with the exception of primers; distributing the fluid to the reaction chambers comprising the primers therein; and, rotating the rotatable circular cartridge to successively bring the contents of each reaction chamber to the different temperatures defined by the distinct zones of the heating plate, wherein the single-stranded DNA is amplified.

In some embodiments of the method, wherein the heating plate has at least three distinct zones that can be heated to at least three different temperatures, the method includes rotating the rotatable circular cartridge to successively bring the contents of each reaction chamber to the at least three temperatures defined by the at least three distinct zones of the heating plate.

The following examples further illustrate the invention but, of course, should not be construed as in any way limiting its scope.

Example 1

This example demonstrates determining the retention level of various microporous hydrophilic nylon membranes when tested at a constant flow rate.

Figure 2:
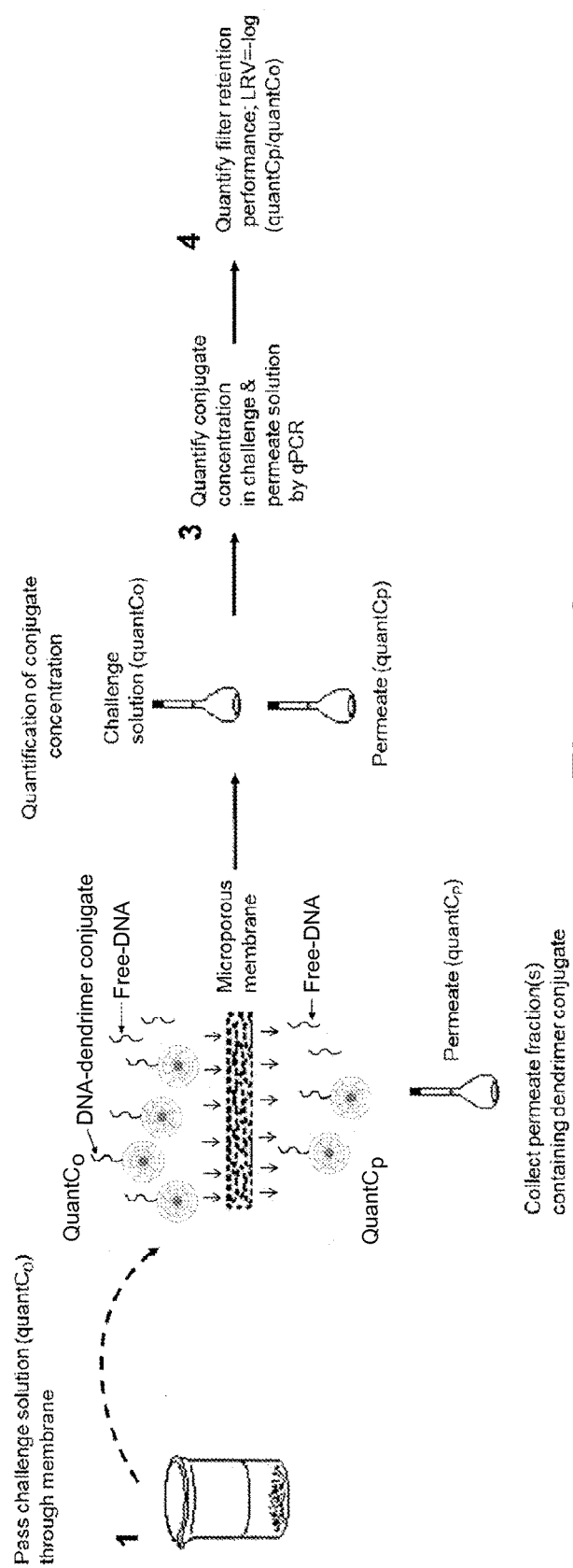
FIG. 2 illustrates a general method according to an embodiment of the present invention.

FIG. 2 shows a general diagrammatic overview of the method carried out in this Example.

Commercially available monodispersed size $5^{th}$ generation polyamidoamine (PAMAM) dendrimer particles with diameters of 5.4 nm (Sigma-Aldrich Chemicals) are activated with n-hydroxysuccinimide to produce ester groups on the dendrimer surface. The activated dendrimer is reacted with a carboxylic terminated 66 base long single-stranded DNA sequence (from 5' to 3') CTTGCAAATCGT-TCTTTGGGTCCTCTTGCGACCCTGGGAGTGAGCTT-GTATGGTTG ACGCCGGATT (SEQ ID:1) to immobilize the DNA on the dendrimer with a 1:1 ratio by covalent amide bond. At pH 7.0, amine groups on the dendrimer are protonated as $NH_3^+$ and are about twice the amount of negatively charged phosphate groups on DNA, thus making the dendrimer conjugate positively charged. Movement of the dendrimer conjugate at neutral pH only from the positive side to the negative side of the electrode during polyacrylamide gel electrophoresis confirms the 1:1 ratio of DNA to dendrimer.

Free-DNA is removed by dialyzing the conjugate solution twice at pH 10.2 using a 100 KDa cutoff membrane.

DNA-dendrimer conjugate stock is spiked in 1 mM CAPS buffer (pH 10.5) to prepare a working challenge solution with a conjugate concentration of $1 \times 10^8$ particle/mL.

A 47 mm microporous nylon filter disc is wetted with 1 mM CAPS (pH 10.5) buffer, the filter disc is placed in a filter holder, a pressure syringe is filled with an appropriate volume of working challenge solution, and tubing is attached to the syringe with a pressure vessel connected through an air valve.

The challenge test is initiated by regulating the pressure to maintain a constant flow rate of 5 mL/min, and multiple permeate fractions each with 10 mL volumes are collected.

5 different nylon filter discs with different pore rating values are tested: 40 nm, 20+250 nm (dual layer), 20 nm, 10 nm, and 5 nm.

DNA standards ranging from $1 \times 10^{11}$ copy/mL to $1 \times 10^3$ copy/mL are prepared by serially diluting DNA (the same DNA sequence as attached to dendrimer) in ultrapure water. The appropriate volume of qPCR reaction mixture (containing master mix (the master mix including a reference dye, polymerase, $MgCl_2$, and dNTPs), primers, and ultrapure water) according to the number of samples, standards, and negative controls is also prepared. 5 μL of working challenge solution and permeate fractions (using the second permeate fraction to avoid any buffer dilution effect on the first permeate fraction) are each added in separate 20 μL qPCR mixtures, and placed in specific wells in a 96 well plate. 5 μL of ultrapure water is added to the negative control wells.

The following sequences are used for carrying out qPCR: Forward primer: CTTGCAAATCGTTCTTTGGG (SEQ ID:2); Reverse primer: AATCCGGCGTCAACCATAC (SEQ ID:3); and Probe: CCTCTTGCGACCCTGGGAGT-GAGCT (SEQ ID:4), wherein the fluorescent dye fluorescein (FAME) is attached to the 5' end of the probe, and the quencher black hole quencher-1 (BHQ1) is attached to the 3' end of the probe.

The 96 well plate is placed in an qPCR machine (7500 Fast Real-Time PCR System; Applied Biosystems, Carlsbad, Calif.) and 40 cycles of qPCR are performed (95° C. for 15 seconds and 60° C. for 60 seconds), and a fluorescence curve is generated from each well with a specific threshold cycle.

The software matches the threshold cycles of a known DNA standard with the threshold cycles of working challenge and permeate solutions to calculate dendrimer conjugate concentration in those solutions (as the 1:1 ratio of DNA to dendrimer allows the qPCR measured DNA concentration to be directly correlated to the concentration of dendrimer particles). The data is analyzed to quantify conjugate concentration in challenge solution and permeate fractions and calculate media performance.

The membrane performance is calculated by taking an inverse log of the concentration of dendrimer conjugate in the permeate to the concentration of dendrimer conjugate in the working challenge solutions.

Figure 3:
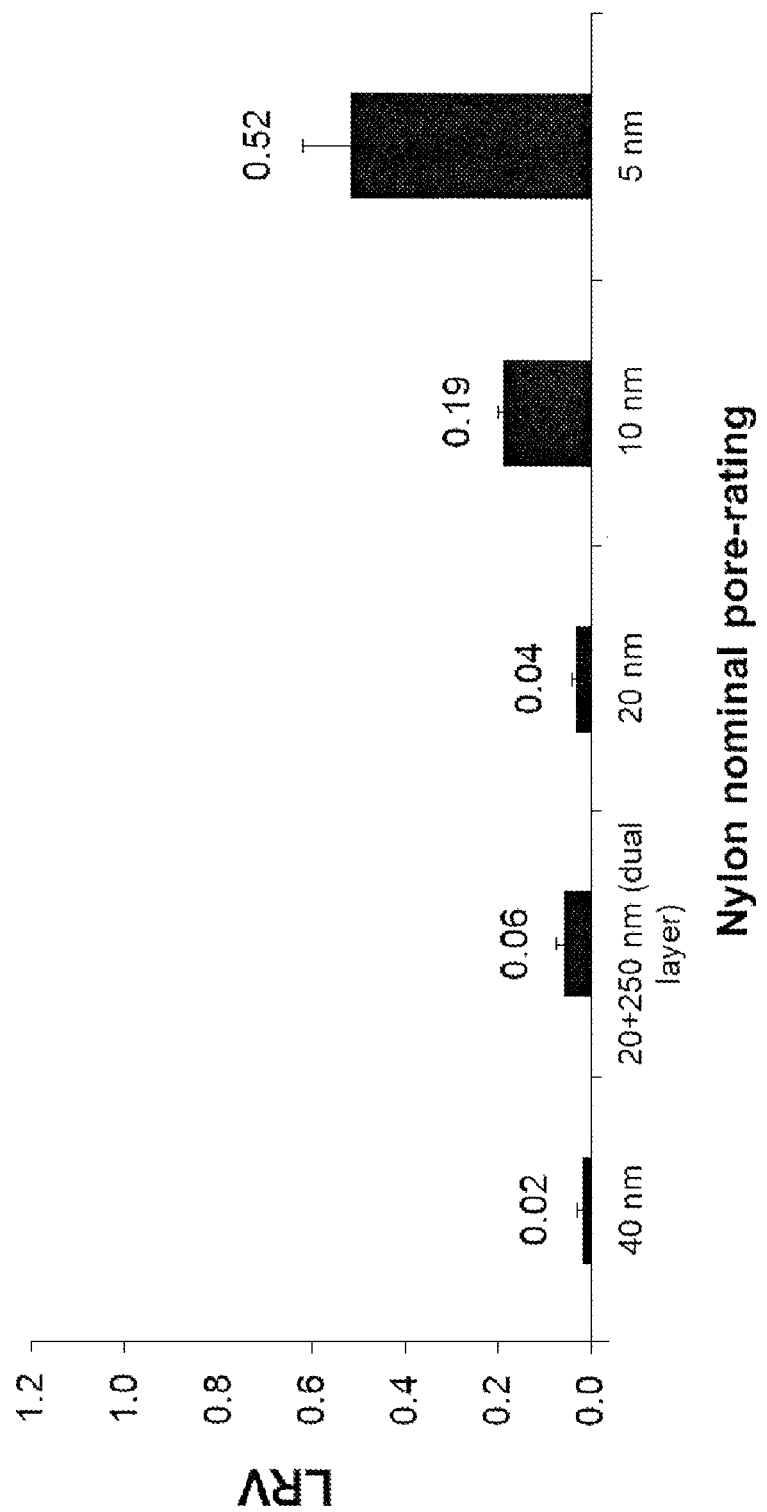
FIG. 3 shows the results of retention tests at a constant flow rate of 5 mL/min using various microporous nylon media with different nominal pore rating values.

As shown in FIG. 3, the respective mean log removal values (LRVs) of the 40 nm, 20+250 nm (dual layer), 20 nm, 10 nm, and 5 nm media are 0.02±0.01, 0.06±0.02, 0.04±0.01, 0.19±0.01, and 0.52±0.10.

The higher than 95% passage of conjugates through larger pore-rated nylon media (e.g., 40 nm, 250+20 nm, 20 nm) suggests that conjugates do not adsorb or stick to the media. Accordingly, the retention values for the finer pore-rated nylon media (e.g., 10 nm and 5 nm) are significantly due to a sieving effect. The results also indicate that the conjugate test at a constant flow rate is able to discriminate between different fine pore-rated nylon media.

Example 2

This example demonstrates determining the retention level of a microporous hydrophobic high density polyethylene (HDPE) membrane when tested at a constant flow rate.

Dendrimer conjugates are prepared as described in Example 1.

DNA-dendrimer conjugate stock is spiked in 1 mM CAPS buffer (pH 10.5) containing 0.03% Tween-20 (a surfactant) to prepare a working challenge solution with a conjugate concentration of 1×10$^8$ particle/mL.

A 47 mm microporous HDPE filter disc is wetted with isopropyl alcohol (IPA), placed in a filter holder, and 150 mL of IPA is passed through the disc at 50 psi to prime the disc, followed by 500 mL of deionized (DI) water to wash the disc.

20 mL of 1 mM CAPS buffer (pH 10.5) containing 0.03% Tween-20 is passed through the disc.

A pressure syringe is filled with an appropriate volume of working challenge solution, and tubing is attached to the syringe with a pressure vessel connected through an air valve.

The challenge test is initiated by regulating the pressure to maintain a constant flow rate of 5 mL/min, and multiple permeate fractions each with 10 mL volumes are collected.

4 different HDPE filter discs with different pore rating values are tested: 30 nm, 10 nm, 5 nm, and 2 nm.

5 μL of working challenge solution and permeate fractions (using the third permeate fraction to avoid any buffer dilution effect on the first or second permeate fractions) are each added in separate 20 μL qPCR mixtures, and placed in specific wells in a 96 well plate. 5 μL of ultrapure water is added to the negative control wells.

qPCR is carried out, and membrane performance is calculated as described in Example 1.

Figure 4:
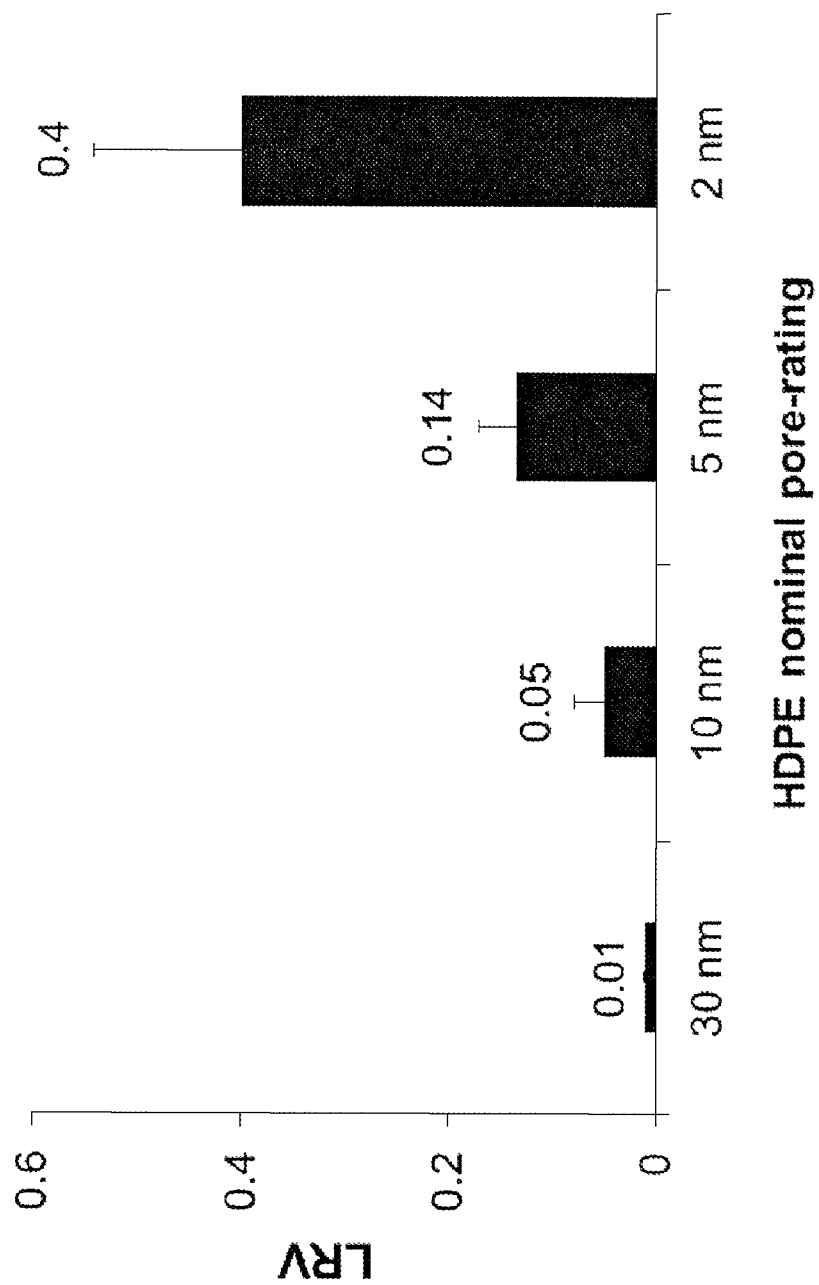
FIG. 4 shows the results of retention tests at a constant flow rate of 5 mL/min using various microporous high density polyethylene media with different nominal pore rating values.

As shown in FIG. 4, the respective mean LRVs of the 30 nm, 10 nm, 5 nm, and 2 nm media is 0.01±0.001, 0.05±0.03, 0.14±0.04, and 0.40±0.15.

The higher than 95% passage of conjugates through the larger pore-rated HDPE (e.g., 30 nm) suggests that conjugates do not adsorb or stick to HDPE media. Accordingly, the retention values for the finer pore-rated HDPE (e.g., 10 nm, 5 nm, and 2 nm) are significantly due to a sieving effect. The results also indicate that the conjugate test at a constant flow rate is able to discriminate between different fine pore-rated HDPE media.

Example 3

This example demonstrates determining the retention level of a microporous hydrophilic nylon membrane when tested at a constant pressure.

Microporous nylon membranes are tested as generally described in Example 1, except that the challenge test is initiated by maintaining the regulator at a fixed pressure of 5 psi, providing a flow rate of 1 mL/min.

Figure 5:
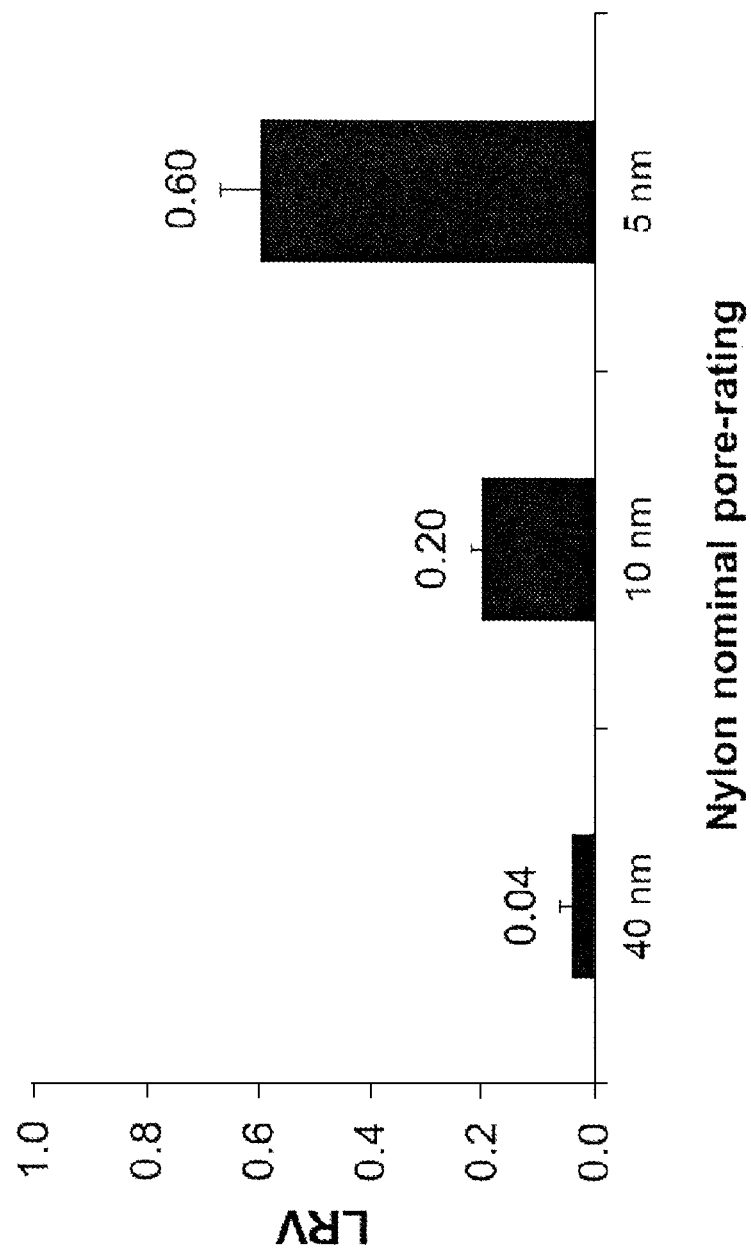
FIG. 5 shows the results of retention tests at a constant pressure of 5 psi using various microporous nylon media with different nominal pore rating values.

As shown in FIG. 5, the respective mean LRVs of the 40 nm, 10 nm, and 5 nm media are 0.04±0.02, 0.20±0.02, and 0.60±0.07.

The higher than 95% passage of conjugates through larger pore-rated nylon media (e.g., 40 nm) suggests that conjugates do not adsorb or stick to the media. Accordingly, the retention values for the finer pore-rated nylon media (e.g., 10 nm and 5 nm) are significantly due to a sieving effect. The results also indicate that the conjugate test at a constant pressure is able to discriminate between different fine pore-rated nylon media.

Example 4

This example demonstrates determining the retention level of a microporous polyaryl sulfone (PAS) membrane when tested at a constant pressure.

A PAS membrane is tested as generally described in Example 3. 2 different PAS filter discs with different pore rating values are tested: 30 nm and 10 nm.

Figure 6:
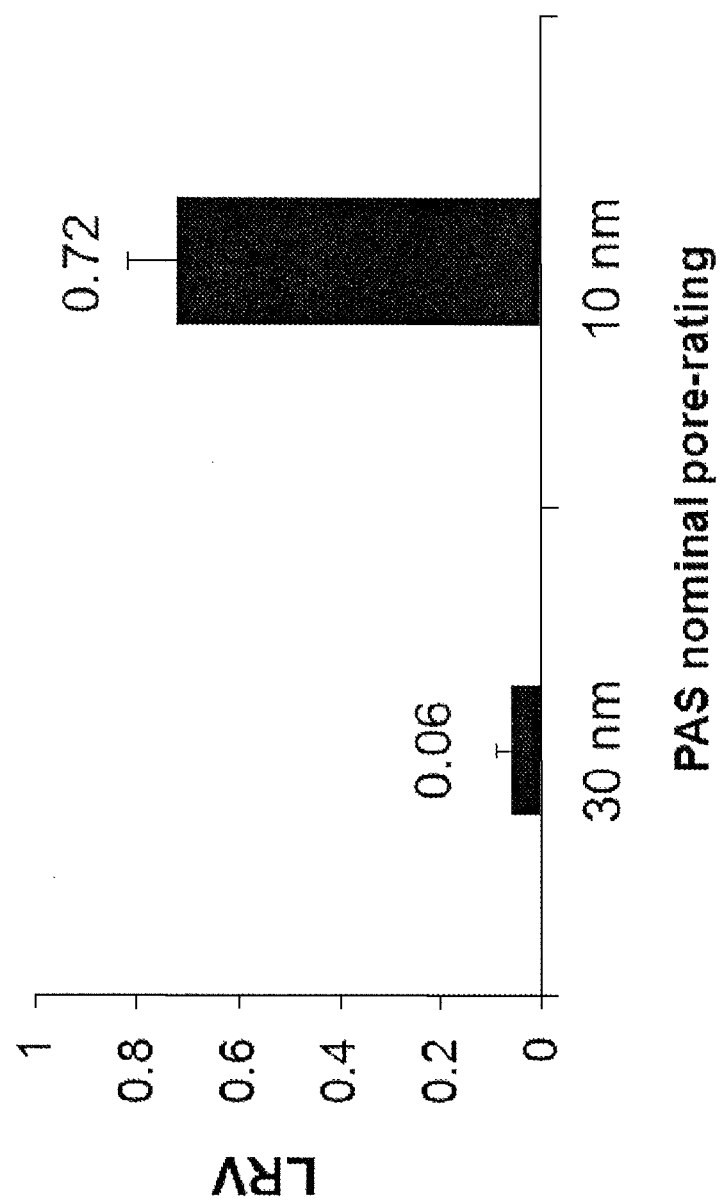
FIG. 6 shows the results of retention tests at a constant pressure of 5 psi using various microporous polyaryl sulfone media with different nominal pore rating values.
Figure 7:
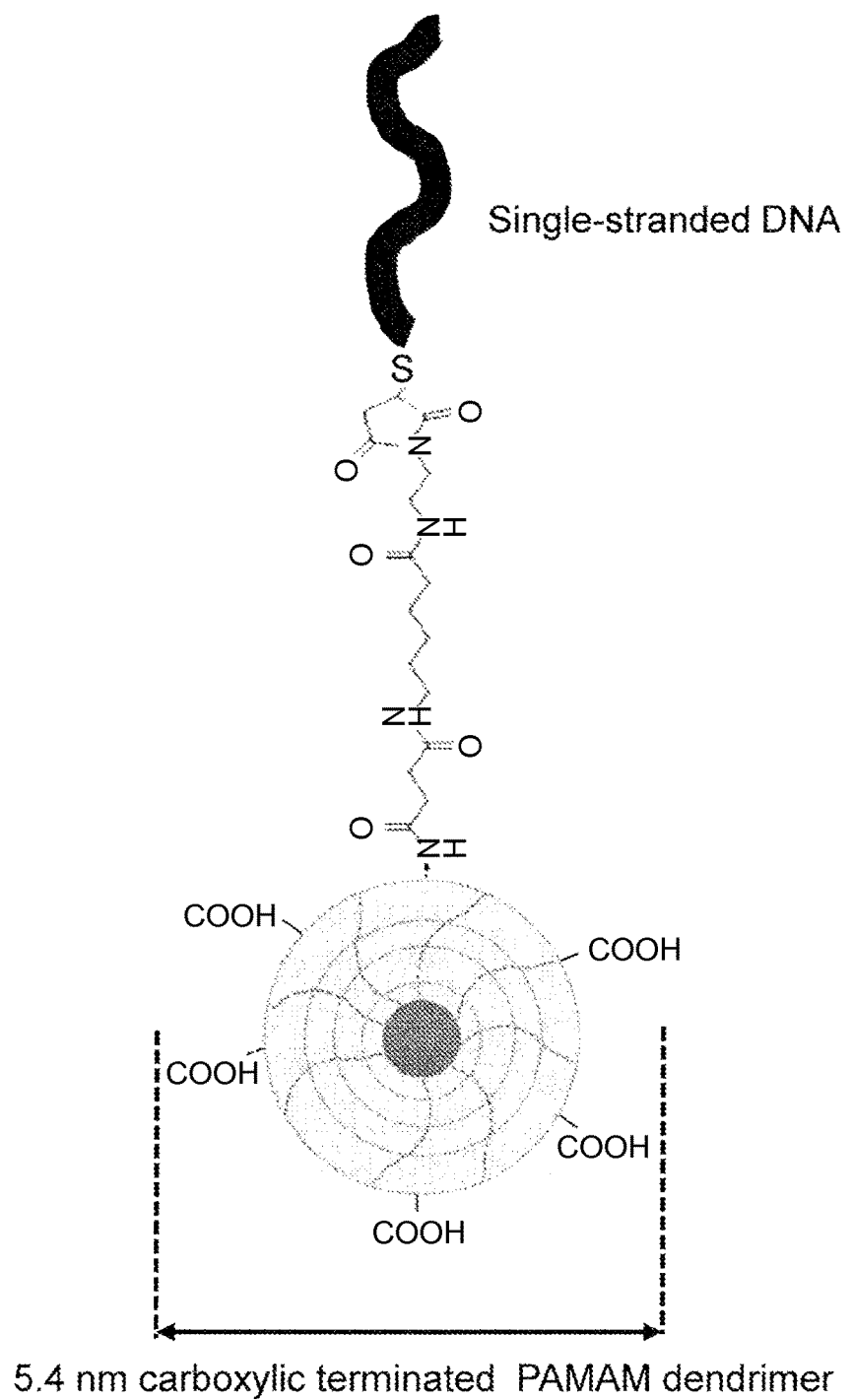
FIG. 7 shows an illustrative dendrimer conjugate comprising a dendrimer particle (illustrated as having a diameter of 5.4 nm) conjugated to single-stranded DNA by a maleimide-thiol bond according to an embodiment of the present invention.

As shown in FIG. 6, the respective mean LRVs of the 30 nm and 10 nm media are 0.06±0.03 and 0.72±0.09.

The higher than 95% passage of conjugates through the larger pore-rated PAS medium (30 nm) suggests that conjugates do not adsorb or stick to the media. Accordingly, the retention value for the finer pore-rated medium (10 nm) is significantly due to a sieving effect. The results also indicate that the conjugate test at a constant pressure is able to discriminate between different pore-rated media.

Example 5

This example demonstrates another carboxylic functionalized PAMAM dendrimer can be used in embodiments of the invention.

Commercially available monodispersed size $5^{th}$ generation polyamidoamine (PAMAM) dendrimer particles with diameters of 5.4 nm (Sigma-Aldrich Chemicals) are activated with a heterobifunctional crosslinker containing amine-reactive succinimidyl ester (i.e., NHS ester) at one end and a sulfhydryl-reactive group (e.g., maleimide) on the other end. A sulfhydryl-terminated oligo is covalently immobilized on the dendrimer in a 1:1 ratio via a maleimide-thiol bond, using SEQ ID:1 as described in Example 1.

Free-DNA is removed by dialyzing the conjugate solution twice at pH 10.2 using a 100 KDa cutoff membrane.

The Example is carried out as generally described in Example 1, using a nominal 10 nm pore rated nylon membrane.

Figure 8:
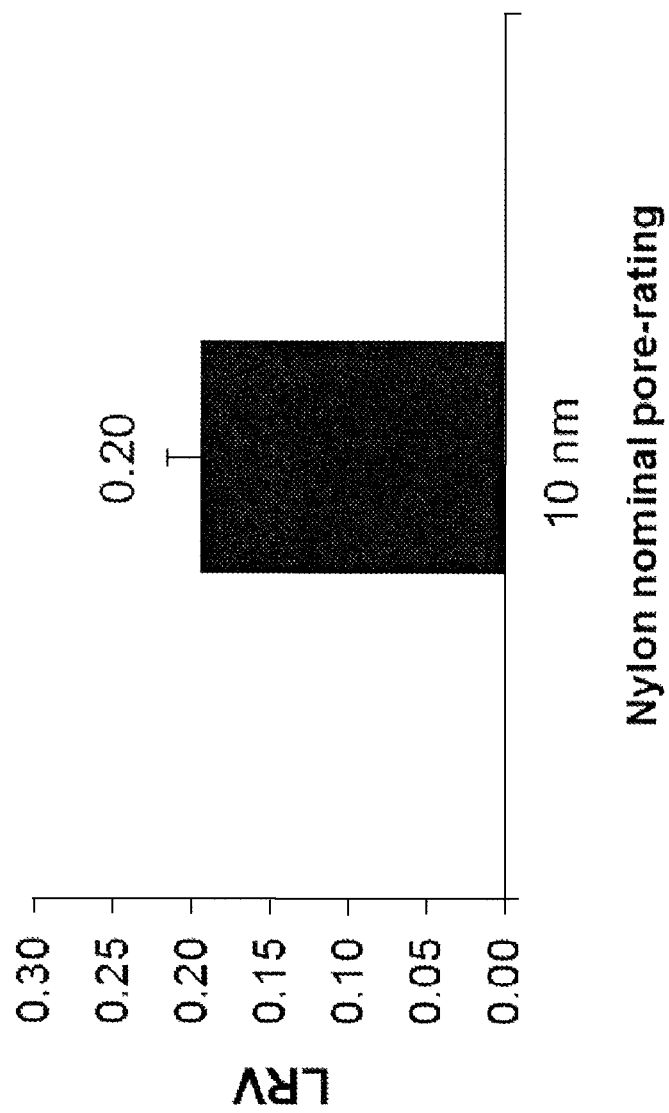
FIG. 8 shows the results of retention tests at a constant flow rate of 5 mL/min using another dendrimer conjugate chemistry and a microporous nylon medium.

As shown in FIG. 8, the mean LRV is 0.20±0.02, confirming the 10 nm pore rating of the membrane. The result shows that retention value is only dependent on conjugate size and not on the nature of conjugate sequence, functionality, and type of DNA-dendrimer bond.

Example 6

This example demonstrates that another single-stranded DNA sequence can be used in accordance with an embodiment of the invention.

An activated dendrimer is prepared as described in Example 1, and reacted with the following carboxylic terminated long single-stranded DNA sequence (from 5' to 3') derived from the genome of a bacterium, *Alicyclobacillus acidocaldarius*: CTTGCTGGACAGTGACTGACTCCACGCCGTAAACGATGAGTGCTAGGTGTGGAAACCCAATAAGCAGTCCGGG (SEQ ID:5) to immobilize the DNA on the dendrimer with a 1:1 ratio by covalent amide bond.

The Example is carried out as generally described in Example 1, using a nominal 10 nm pore rated nylon membrane.

The following sequences are used for carrying out qPCR:
Forward primer:
CTTGCTGGACAGTGACTGAC (SEQ ID:6); Reverse primer:
CCCGGAGTGCTTATTGGGTTTCC (SEQ ID:7); and Probe:
CCACGCCGTAAACGATGAGTGCTAGGTG (SEQ ID:8), wherein the fluorescent dye fluorescein (FAME) is attached to the 5' end of the probe, and the quencher black hole quencher-1 (BHQ1) is attached to the 3' end of the probe.

Figure 9:
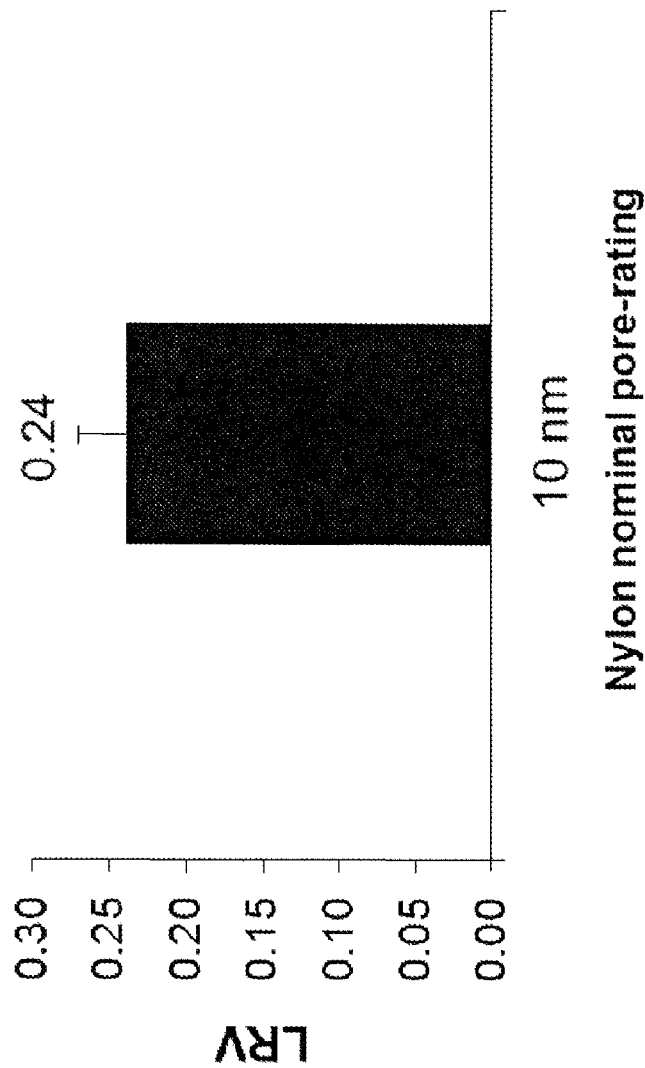
FIG. 9 shows the result of a retention test at a constant flow rate of 5 mL/min using another sequence with a dendrimer and a microporous nylon medium.

As shown in FIG. 9, the mean LRV is 0.24±0.01, confirming the 10 nm pore rating of the membrane. The result shows that retention value is only dependent on conjugate size and not on the nature of conjugate sequence, functionality, and type of DNA-dendrimer bond. This is also reinforced by the similar results, referring to 10 nm pore rated nylon membranes, as shown in FIGS. 3 and 8.

Example 7

This example demonstrates determining the retention level of various microporous polyaryl sulfone (PAS) membranes when tested at a constant flow rate.

PAS membranes are tested as generally described in Example 1. 2 different PAS filter discs with different pore rating values are tested: 30 nm and 10 nm.

Figure 10:
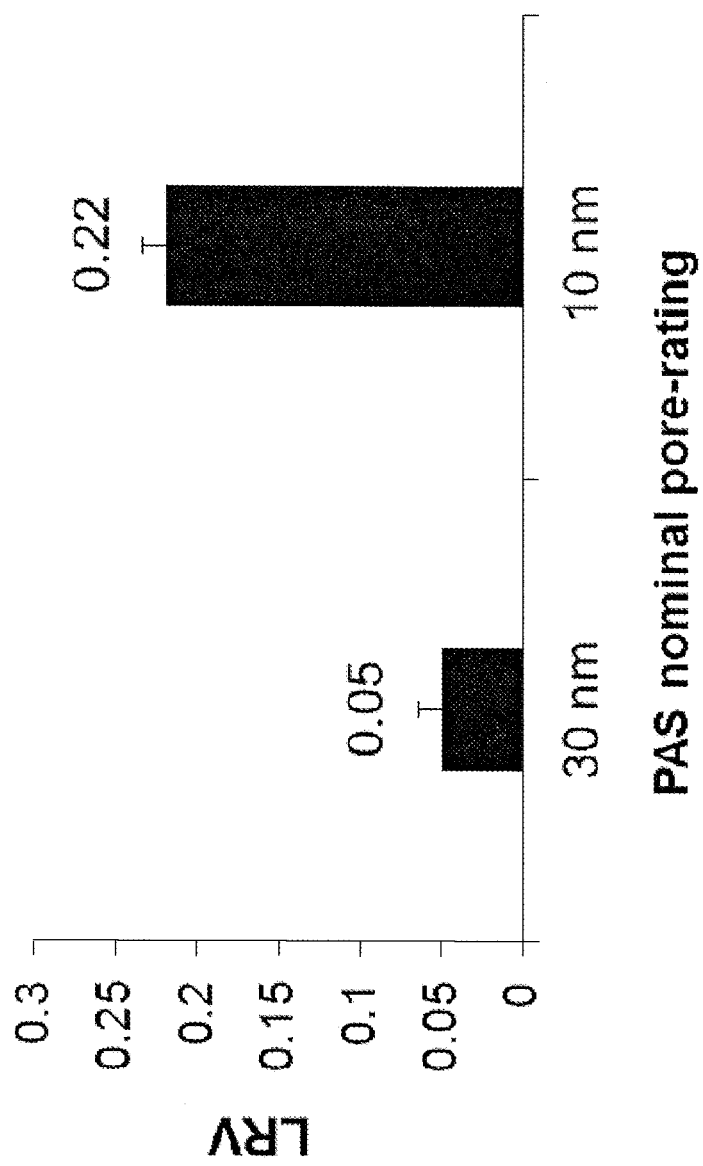
FIG. 10 shows the results of retention tests at a constant flow rate of 5 mL/min using various microporous polyaryl sulfone media with different nominal pore rating values.

As shown in FIG. 10, the respective mean LRVs of the 30 nm and 10 nm media are 0.05±0.01 and 0.22±0.01.

The higher than 95% passage of conjugates through the larger pore-rated PAS medium (30 nm) suggests that conjugates do not adsorb or stick to the media. Accordingly, the retention value for the finer pore-rated medium (10 nm) is significantly due to a sieving effect. The results also indicate that the conjugate test at a constant pressure is able to discriminate between different pore-rated media.

Example 8

This example demonstrates that a variety of dendrimer conjugate concentrations can be used to analyze membranes in embodiments of the invention, and that the test represents sieving performance.

An activated dendrimer is prepared and reacted with a carboxylic terminated long single-stranded DNA sequence as generally described in Example 1.

5 different DNA-dendrimer conjugate challenge concentrations are prepared, and the Example is generally carried out at a constant flow rate of 5 mL/min as generally described in Example 1, using a nominal 10 nm pore rated nylon membrane. The challenge concentrations are $2\times10^4$ particle/mL, $2\times10^5$ particle/mL, $2\times10^6$ particle/mL, $2\times10^7$ particle/mL, and $2\times10^8$ particle/mL.

Figure 11:
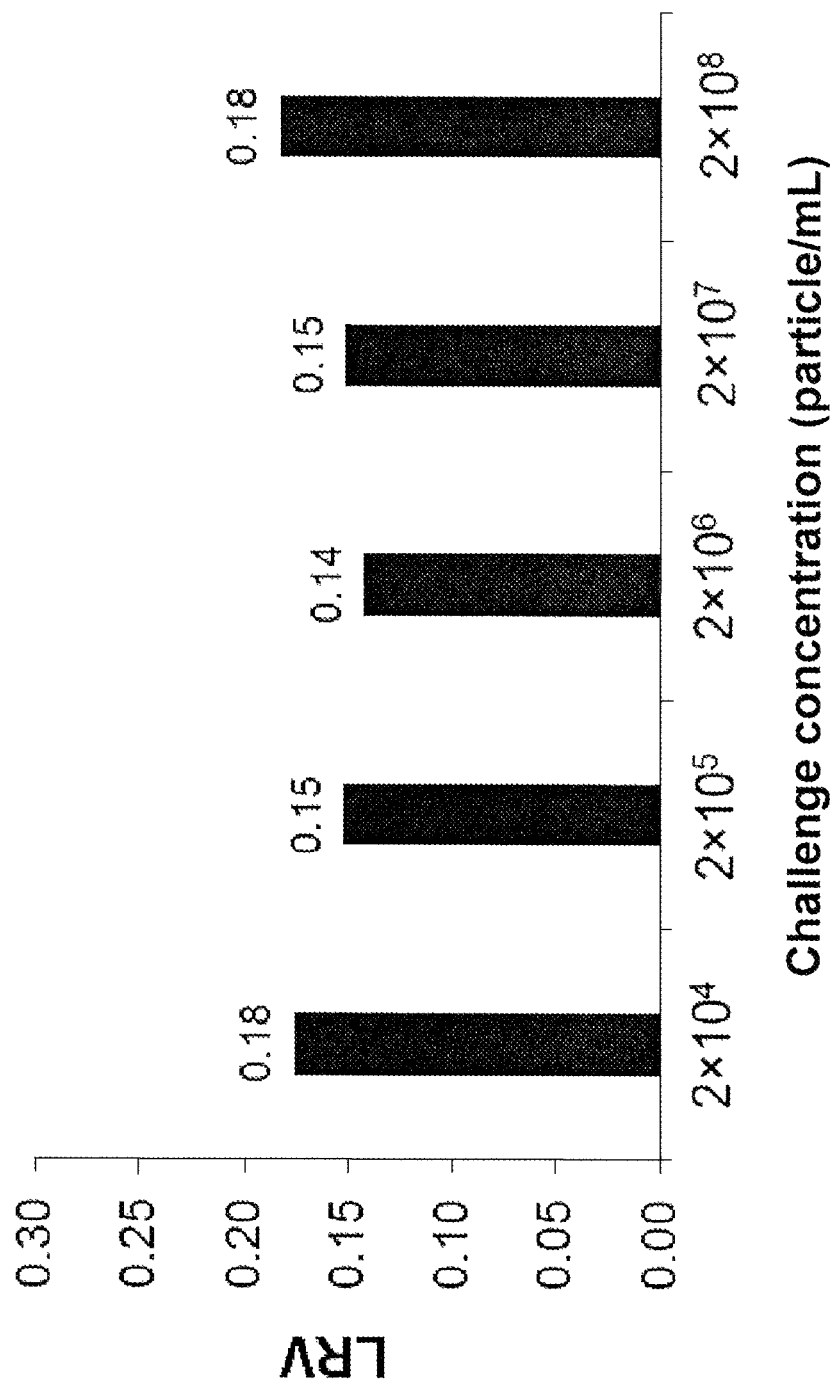
FIG. 11 shows the results of retention tests at a constant flow rate of 5 mL/min using various challenge concentrations of conjugates.

As shown in FIG. 11, the LRVs for $2\times10^4$ particle/mL, $2\times10^5$ particle/mL, $2\times10^6$ particle/mL, $2\times10^7$ particle/mL, and $2\times10^8$ particle/mL challenge concentration are respectively, 0.18, 0.15, 0.14, 0.15, and 0.18.

The results confirm the 10 nm pore rating of the membrane, and show that the test is independent of particle challenge concentration, representing true sieving performance of the media. Additionally, quantification of such a low conjugate concentration is only possible by qPCR.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method for determining retention level and/or pore structure of a membrane, the method comprising:
   (a) passing a challenge solution comprising single-stranded DNA conjugated to dendrimers (dendrimer conjugates), through a microporous membrane, to provide a permeate solution comprising the dendrimer conjugates;
   (b) obtaining equal volumes of:
      i. the challenge solution comprising dendrimer conjugates; and,
      ii. the permeate solution comprising dendrimer conjugates;
   (c) combining (i) with PCR reagents to provide a challenge solution/PCR mix, and combining (ii) with PCR reagents to provide a permeate solution/PCR mix;
   (d) performing a plurality of PCR cycles using each of the challenge solution/PCR mix, and the permeate solution/PCR mix, to amplify the single-stranded DNA;
   (e) measuring single-stranded DNA concentration, which correlates to dendrimer conjugate concentration;
   (f) quantifying the dendrimer conjugate concentration in the challenge solution (quantCo); and
   quantifying the dendrimer conjugate concentration in the permeate solution (quantCp);
   and,
   (g) determining the retention level and/or pore structure of the membrane based on a comparison of the quantCp to the quantCo.

2. The method of claim 1, wherein the PCR cycles are qPCR cycles.

3. The method of claim 2, wherein (g) comprises comparing log reduction values for quantCp and quantCo.

4. The method of claim 2, wherein the dendrimer conjugates have a 1:1 ratio of single-stranded DNA to dendrimer.

5. The method of claim 2, comprising passing the challenge solution through the microporous membrane at a constant flow rate.

6. The method of claim 2, comprising passing the challenge solution through the microporous membrane at a constant pressure.

7. The method of claim 2, wherein (c) and (d) comprise using a device comprising a rotatable circular cartridge having a plurality of reaction chambers, and a reservoir, the reaction chambers being connected to the reservoir via channels, wherein at least a portion of the reaction chambers comprise primers; and a heating plate having at least two distinct zones that can be heated to at least two different temperatures, the method comprising:
   at least partially filling the reservoir with a fluid containing dendrimer conjugates and PCR reagents for carrying out an amplification reaction, with the exception of primers;
   distributing the fluid to the reaction chambers comprising the primers therein;
   and,
   rotating the rotatable circular cartridge to successively bring the contents of each reaction chamber to the at least two temperatures defined by the at least two distinct zones of the heating plate, wherein the single-stranded DNA is amplified.

8. The method of claim 1, wherein (g) comprises comparing log reduction values for quantCp and quantCo.

9. The method of claim 8, wherein the dendrimer conjugates have a 1:1 ratio of single-stranded DNA to dendrimer.

10. The method of claim 8, comprising passing the challenge solution through the microporous membrane at a constant flow rate.

11. The method of claim 8, comprising passing the challenge solution through the microporous membrane at a constant pressure.

12. The method of claim 1, wherein the dendrimer conjugates have a 1:1 ratio of single-stranded DNA to dendrimer.

13. The method of claim 1, comprising passing the challenge solution through the microporous membrane at a constant flow rate.

14. The method of claim 1, comprising passing the challenge solution through the microporous membrane at a constant pressure.

15. The method of claim 1, wherein (c) and (d) comprise using a device comprising a rotatable circular cartridge having a plurality of reaction chambers, and a reservoir, the reaction chambers being connected to the reservoir via channels, wherein at least a portion of the reaction chambers comprise primers; and a heating plate having at least two distinct zones that can be heated to at least two different temperatures, the method comprising:
- at least partially filling the reservoir with a fluid containing dendrimer conjugates and PCR reagents for carrying out an amplification reaction, with the exception of primers;
- distributing the fluid to the reaction chambers comprising the primers therein; and,
- rotating the rotatable circular cartridge to successively bring the contents of each reaction chamber to the at least two temperatures defined by the at least two distinct zones of the heating plate, wherein the single-stranded DNA is amplified.

16. The method of claim 15, wherein the heating plate has at least three distinct zones that can be heated to at least three different temperatures, and the method includes rotating the rotatable circular cartridge to successively bring the contents of each reaction chamber to the at least three temperatures defined by the at least three distinct zones of the heating plate.

17. The method of claim 16, wherein at least a portion of the reaction chambers comprise probes in addition to the primers.

18. The method of claim 15, wherein at least a portion of the reaction chambers comprise probes in addition to the primers.

19. A kit for determining retention level and/or pore structure of a membrane comprising:
- a solution comprising a plurality of dendrimers conjugated to single-stranded DNA; a rotatable circular cartridge having a plurality of reaction chambers containing dried primers, and a reservoir, wherein the reaction chambers are connected to the reservoir via channels; and a qPCR master mixture.

20. The kit of claim 19, wherein the reaction chambers further contain dried probes.

* * * * *